United States Patent

Boughner et al.

Patent Number: 5,314,404
Date of Patent: May 24, 1994

[54] TETHERED MEDICAL RESTRAINT DEVICE

[75] Inventors: Robert L. Boughner, Lansing; Robert P. Hubbard, East Lansing, both of Mich.

[73] Assignee: Biomechanical Design, Inc., Okemos, Mich.

[21] Appl. No.: 115,431

[22] Filed: Sep. 1, 1993

Related U.S. Application Data

[60] Division of Ser. No. 975,687, Nov. 13, 1992, Pat. No. 5,242,377, which is a continuation-in-part of Ser. No. 784,571, Oct. 29, 1991, Pat. No. 5,248,293.

[51] Int. Cl.⁵ .............................................. A63B 5/00
[52] U.S. Cl. ........................................ 602/17; 602/36; 128/876
[58] Field of Search ................... 602/17, 18, 19, 36; 128/97.1, 870, 871, 876; 606/241

[56] References Cited

U.S. PATENT DOCUMENTS

| | | |
|---|---|---|
| Re. 32,939 | 6/1989 | Gardner et al. . |
| Re. 32,940 | 6/1989 | Gardner et al. . |
| 1,803,556 | 5/1931 | Nugent . |
| 2,571,461 | 10/1951 | Livingston et al. ............... 602/17 |
| 3,099,261 | 7/1963 | Doss et al. . |
| 3,108,587 | 10/1963 | Das ................................. 602/36 |
| 3,170,659 | 2/1965 | Wood, Jr. . |
| 3,359,976 | 12/1967 | Laval, Jr. . |
| 3,376,064 | 4/1968 | Jackson . |
| 3,397,688 | 8/1968 | Gottfried . |
| 3,522,804 | 8/1970 | Towbin . |
| 3,835,847 | 9/1974 | Smith .............................. 602/36 |
| 3,922,034 | 11/1975 | Eggert . |
| 4,207,881 | 6/1980 | Richter ............................ 602/17 |
| 4,339,151 | 7/1982 | Riggs . |
| 4,451,932 | 6/1984 | Wagemann et al. . |
| 4,477,041 | 10/1984 | Dunne . |
| 4,508,294 | 4/1985 | Lorch . |
| 4,592,523 | 6/1986 | Herndon . |
| 4,638,510 | 1/1987 | Hubbard . |
| 4,664,341 | 5/1987 | Cummings . |
| 4,718,412 | 1/1988 | Nesbitt . |
| 4,899,736 | 3/1990 | Nesbitt . |
| 4,903,711 | 2/1990 | Gunther . |
| 5,010,898 | 4/1991 | de Kanawati et al. .......... 602/17 |
| 5,086,757 | 2/1992 | Lestini ............................. 602/19 |
| 5,129,881 | 7/1992 | Pope ................................ 606/241 |
| 5,199,940 | 4/1993 | Morris et al. .................... 602/17 |

Primary Examiner—Richard J. Apley
Assistant Examiner—Lynne A. Reichard
Attorney, Agent, or Firm—Ian C. McLeod

[57] ABSTRACT

A head and neck support device (10) is described. The device (10) includes a first plate (12) and a second plate (98). The first plate extends along the back of the torso (202) and is strapped to the torso by a torso harness (70). The second plate extends upward from the first plate behind the head (204) and neck (206) of the person (200). A head harness (142) for grasping the head is attached to the device by a tether (148) which is inserted through slots (138C, 140C) in a right and left harness support (138, 140) mounted on the second plate (98). The head harness allows the head to rotate while maintaining the head in a desired position.

8 Claims, 5 Drawing Sheets

TETHERED MEDICAL RESTRAINT DEVICE

This is a divisional of copending application Ser. No. 07/975,687 filed on Nov. 13, 1992, now U.S. Pat. No. 5,242,377 which is a continuation-in-part of Ser. No. 07/784,571 filed Oct. 29, 1991 now U.S. Pat. No. 5,248,293.

BACKGROUND OF THE INVENTION

(1) Field of the Invention

The present invention relates to a head and neck support device for use by persons with a neck dysfunction. Neck dysfunction may result from congenital or acquired disease, trauma, or fatigue. In particular, the present invention relates to a medical restraining device which maintains a desired head position and which decreases neck loads by coupling the head and the torso. The device is comprised of a first plate which is secured to the upper torso and a second plate which is secured to the first plate and extends upwards from the first plate to a position behind the neck and head of the user. In the preferred embodiment, the first plate is comprised of an inner plate and an outer plate which are screwed together. The second plate is preferably attached by a tethering system to a harness as a head grasping apparatus that is worn circumferentially around the head. The head harness includes a forehead strap and a crown or top strap. The head harness facilitates grasping the head so that supportive forces may be applied to the head through the tethers, connected between the head harness and the second plate. The tethering system also partially transfers the weight of the head, held in the head harness, to the second plate mounted on the first plate. That way, the head is supported on the torso, which helps to decrease neck loads, and the head is held to regulate anterior, posterior and sidewards head motion. The first plate is held to the body by a torso harness. The curvature of the first plate and the curvature of the second plate may be varied by a system of turnbuckles which vary the contour of the support device to accommodate a particular head and torso configuration. For cosmetic reasons, the first plate can be worn underneath clothing and a wig or hat can be worn to hide the head harness.

(2) Prior Art

Many persons suffer from neck dysfunction due to the effects of cervical spine trauma, diseases such as cerebral palsy, multiple sclerosis, and muscular dystrophy, or fatigue induced by environmental stress. The result of neck dysfunction is poor head control. The prior art has described various types of devices that relieve neck loads by supporting a person's head on their torso through the use of head rests, under chin supports, of various restraint devices which function by supporting the head and torso with a rigid structure, connected to a seat in which the person is sitting. Head rests control rearward head motions, but do little to control forward and side motions of the head. Head support from below the jaw line does nothing to control rearward head motions while possibly creating difficulties in swallowing, breathing and sanitation. Devices which attempt to fix torso and head positions relative to a seating device fail because total body immobilization is impossible to achieve; inevitably, the torso will move in the seat and the neck is stretched as the head remains fixed relative to the seat. Moreover, none of the prior art devices were intended for daily use by persons suffering neck dysfunction from trauma or disease.

Nugent U.S. Pat. No. 1,803,556 describes a support for the entire spinal column. The device consists of pads at the base of the spine and in between the patient's shoulders. The pads are strapped onto the patient using frontal pads and straps. Rods extend between the back pads and are adjustable in length. L-shaped support rods extend over the shoulders and are connected to the top back pad and strapped onto the patient using the front pad. A head bar extends upward from the top back pad and forms a right angle extending horizontally above the patient's head. The head is held in place by a head strap and a chin strap which are connected to the head bar. This device is cumbersome and conspicuous, thus not intended for everyday or public wear.

Nesbitt U.S. Pat. No. 4,899,736 describes a cervical spine bar. The device has generally a main body portion of corrugated plastic with flanges which are to be folded around a patient and held in place by tabs and straps. The device is intended to be used in emergency situations to immobilize a patient's head, neck and torso to prevent further injury to the cervical spine.

Laval U.S. Pat. No. 3,359,976 describes a portable device for maintaining the back of a vertebral body in traction. The device consists of an inverted U-shaped support member which is secured to the patient's trunk by a pair of identical shoulder straps. A support post extends upward from the support member and an overhead support arm integrally attached to the support post extends forwardly of the patient's head. A spring is attached to the support arm on one end and an orthopedic sling on the other. The patient's head is gripped by the sling which consists of a chin strap and an occipital strap at the back of the head. The device draws the back of the head upwardly and forwardly in longitudinal extension of the spinal column and neck which provides a portable means for maintaining the back of a patient in traction. This device is intended to maintain the patient's head in a specific position allowing no movement.

Wood, Jr. U.S. Pat. No. 3,170,659 describes a head restraint for use in a space vehicle that has a curved rear head support with ear flaps pivotally hinged to each side of the head support. The head support is mounted to a frame connected to a seat or an integral part of the space vehicle. A forehead strap and a chin strap connect between the ear flaps. This invention permits the head to slide inside the rigid back rest and side flaps while the chin and forehead straps pivot and follow the head. That way, when loads are applied to the vehicle causing the occupant to move in the seat, the occupant's neck is not stretched. This device is somewhat complicated and requires that the crewman be occupying a seat.

Gottfried U.S. Pat. No. 3,397,688 describes a pneumatically inflated neck and head stabilizer. The stabilizer device attempts to achieve total immobilization of the head and neck through use of armpit straps as a means of attaching the device to the torso. The immobilizer consists of a helmet or hood for enveloping a patient's head. The helmet is fabricated of sheet material having inflatable pockets that contact the head while the armpit harness holds the helmet in place. This immobilizer device is obtrusive and does not relieve normal load forces placed on the neck as the neck supports the head.

Towbin U.S. Pat. No. 3,522,804 describes an infant's neck and head support that is intended to prevent spinal injuries of the hyperextension or "whiplash" type, caused by sudden and extreme movement of the head. The support is made of molded rubber and extends over the child's shoulders, back and chest. A head support, shaped to conform to the child's head, extends upwards along the back of the infant's neck and head and is reinforced by stiffening ribs. This device controls only rearward head motions and was intended to be worn continuously during the first four months of life. This device does not use a tethering system to control head motion and does not help to relieve normal load forces placed on the neck as the neck supports the head. Also, this device tends to make it difficult for an infant to swallow.

Riggs U.S. Pat. No. 4,339,151 describes a head restraint for supporting the head while a user is seated in a chair. The head restraint has a strap that is wrapped around the back of a chair and an adjustable headband secured to a central, forward portion of the strap. The headband is worn on the user's head for supporting the head. This device requires that the user be seated in the chair, is very noticeable and the device does not relieve normal load forces placed on the neck as the neck supports the head.

Wagemann et al U.S. Pat. No. 4,451,932 describes a device intended for use in infants, especially premature infants. The device functions to produce total, temporary restraint of all limbs and the head during extensive medical procedures. The device is also classified as an article of chill reducing clothing.

Nesbitt U.S. Pat. No. 4,718,412 describes a single use, emergency care cervical immobilization means comprised of a lightweight cervical spine board made of wax coated or plastic coated reinforced double walled corrugated board. The device has pre-cut score lines for folding the device around the sides of the head and around the sides of the body to substantially enclose the wearer's neck and throat. The device is primarily used to immobilize the human head, neck and torso for use in emergency situations to prevent further injury to a potentially injured cervical spine.

Gunther U.S. Pat. No. 4,903,711 describes a device for preventing infant colic and stomach discomfort. The device has a vest that is worn by the infant during feeding and burping. A bubble level is attached to the vest for visually indicating the position of the infant's torso with respect to vertical. This is a cumbersome device that completely encircles the neck and that is required to be worn externally over the infant's clothing.

Hubbard U.S. Pat. No. 4,638,510 describes a device intended for use by occupants and drivers of high performance vehicles to reduce motions or loading in the neck and the upper torso when the vehicle experiences sudden deceleration or acceleration. The device has a stiff yoke worn over the upper torso of the occupant and a high collar that extends upwards from the yoke, with a set of tethers connected between the lateral and rear portions of a helmet and the collar. The collar extends upwards to adjacent the center of gravity of the head and helmet which is at about eye level of the occupant. The tethers allow needed head movement and yet reduce the potential for fatigue and crash injury by carrying forces that would otherwise be transmitted through the neck, thus reducing extreme motions of the head.

Other patents describe restraining devices that are mounted to a seat of a high performance vehicle and clasp the head of the occupant to limit head motion relative to the seat. These include Jackson U.S. Pat. No. 3,376,064; Eggert U.S. Pat. No. 3,922,034; Dunne U.S. Pat. No. 4,477,041; Cummings U.S. Pat. No. 4,664,341; British Patent No. 656,079 to Bower and British Patent No. 978,422 to Fitzgerald and Fisher.

Other U.S. patents distantly related to the present invention include Doss et al U.S. Pat. No. 3,099,261; Lorch U.S. Pat. No. 4,508,294; and Herndon U.S. Pat. No. 4,592,523.

What is needed is a device that can be worn by both ambulatory people and people confined to a chair and that regulates anterior, posterior and sidewards head motion and that further helps to partially relieve neck loads by coupling the head with the torso. That way, when the load carrying capacity of the neck is altered by muscle fatigue, disease or through traumatic damage to the cervical vertebrae, the person is still able to maintain an acceptable head position during daily activities.

OBJECTS

It is therefore an object of the present invention to provide a device that maintains a desired head position and that partially decreases neck loads by coupling the head and the torso. Further, it is an object of the present invention to provide a head and neck stabilization device that provides head and neck support in persons unable to do so through their muscle strength and coordination, so that such persons are able to maintain acceptable head position during daily activities or transportation. Still further, it is an object of the present invention to provide a device that is worn beneath the clothing of both ambulatory persons and persons confined to a chair or seat and that helps to hold the head in an upright position to regulate anterior, posterior and sidewards head motion by coupling the head and the torso. Finally, it is an object of the present invention to provide a device for supporting the head and neck during daily activities that is relatively simple to construct and inexpensive to manufacture. These and other objects will become increasingly apparent by reference to the following description and to the drawings.

DETAILED DESCRIPTION OF THE PREFERRED EMBODIMENT

The present invention relates to a head support device to be worn by a person to maintain desired head positions relative to the torso of the person which comprises: a bendable support means, which can be secured to the torso along the backbone of the person and having a portion of the support means extending behind the head of the person and which is adjustable by bending to a desired contour along the backbone of the person; strap means mounted on the support means for securing the support means to the torso; a head harness means attached to the support means behind the head, which is securable around the head to provide a secure means of holding the head in position to provide the desired head positions; and tensioning means for bending the support means mounted along the support means.

Furthermore, the present invention relates to a head support device to be worn by a person to maintain desired head positions relative to the torso, which comprises: a bendable, first plate means to be mounted along the backbone of the person and which is adjustable by bending to a desired contour along the backbone of the person; a bendable, second plate means mounted on the first plate means and extending upwards to a position adjacent a rear portion of the head of the person and which is adjustable by bending to a desired contour along the neck of the person; tensioning means for bending the first and second plate means and mounted on both the first and second plate means; and a head harness means attached to the second plate means which is securable around the head to provide a secure means of holding the head to provide the desired head positions.

Also, the present invention relates to a head support device to be worn by a person to maintain a desired head position, which comprises: a bendable first plate means which can be secured along the backbone of the person and which is adjustable by bending to a desired contour along the backbone of the person; a bendable, second plate means mounted on the first plate means and extending upwards to a position adjacent a rear portion of the head of the person and which is adjustable by bending to a desired contour along the neck of the person; tensioning means for bending the first and second plate means and mounted on both the first and second plate means; and a head harness attached to the second plate means, which is securable around the head to provide a secure means of holding the head in a position to provide the desired head position, the harness including tether means on either side of the head and extending between the head harness means and the second plate means to attach the head harness to the second plate means to support the head in the desired head position.

Further, the present invention relates to a method for providing a head support using a device to be worn by a person to maintain desired head positions relative to the torso of the person which comprises: a bendable support means, which can be secured to the torso along the backbone of the person and having a portion of the support means extending behind the head of the person and which is adjustable by bending to a desired contour along the backbone of the person; strap means mounted on the support means for securing the support means to the torso; a head harness means attached to the support means behind the head, which is securable around the head to provide a secure means of holding the head in position to provide the desired head positions; and tensioning means for bending the support means mounted along the support means, which method comprises: adjusting the contour of the support means with the tensioning means; securing the bendable support means to the torso with the strap means; and mounting the head harness means around the head of the person so that the support means and head harness means are in the desired head positions.

Finally, the present invention relates to a head harness means for a head support device to be worn by a person to maintain a desired head position relative to a support means which is mounted on the torso of the person to which the harness means is secured, which comprises: a tether means connected between the head harness and the support means adjacent to the center of gravity of the head, to support the head in a desired position, wherein the harness is slideably mounted in a pocket in the head harness adjacent to the forehead of the person so that the head can be moved side to side on the neck.

Figure 1:
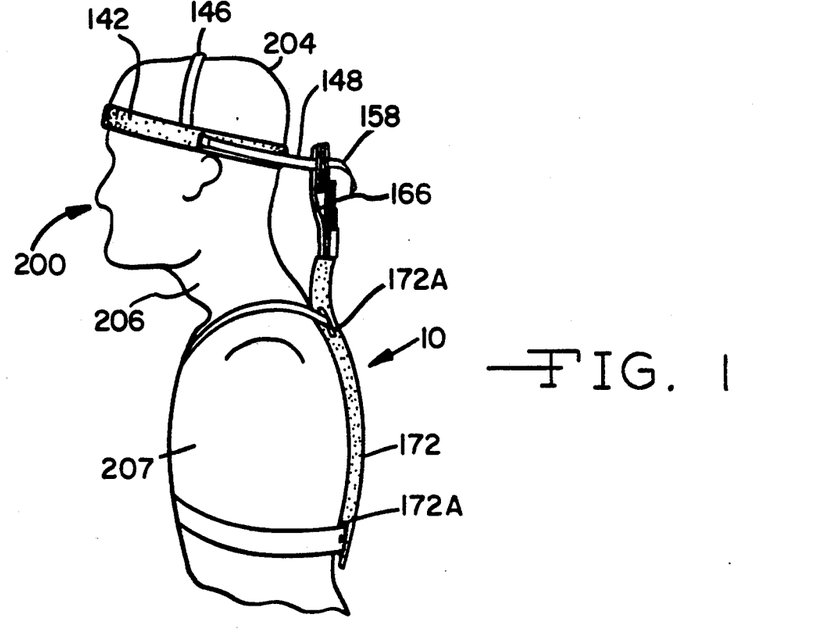
FIG. 1 is a side view of the support device 10 being worn by a person 200.

FIGS. 1 to 9 show the preferred embodiment of the head support device 10. FIG. 1 shows the support device 10 adapted to be strapped to the torso 202 of a person 200 suffering from neck dysfunction for support of the head 204 and neck 206 on the torso 202 so that the head 204 is maintained in an upright position for daily activities. The support device 10 comprises a bendable first plate 12 and a bendable second plate 98. The first plate 12 and the second plate 98 are preferably made of a resilient plastic material such as cellulose acetate butyrate, which can be purchased as GEMEX CAB TM, from Gemini, Canon Falls, Minn.

Figure 6:
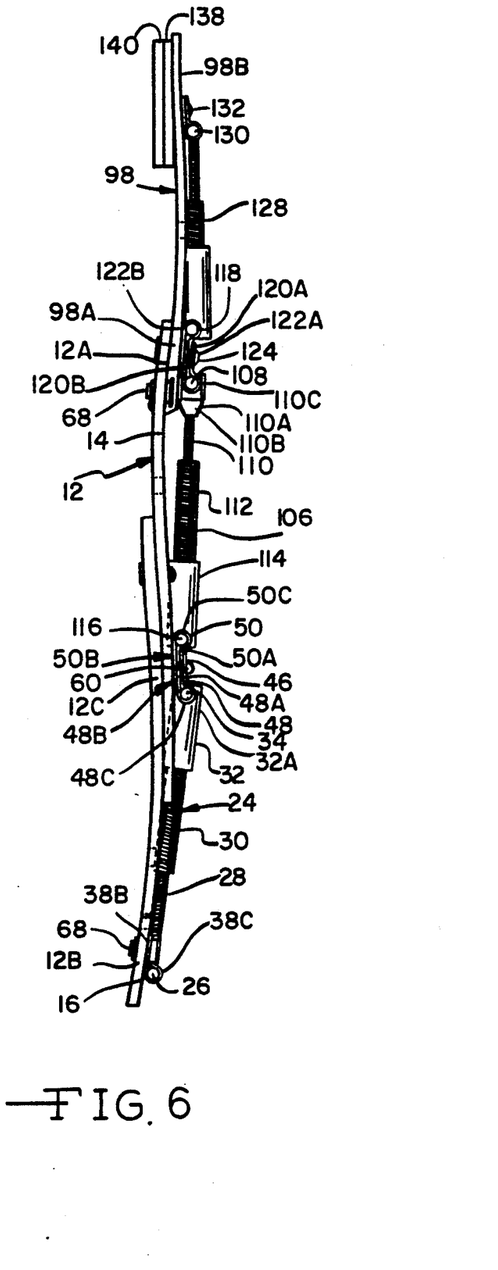
FIG. 6 is a side view of the support device 10 showing the inner plate 16 and outer plate 14 of the first plate 12 and the right harness support 138 and left harness support 140 of the second plate 98.
Figures 7, 8, 9:
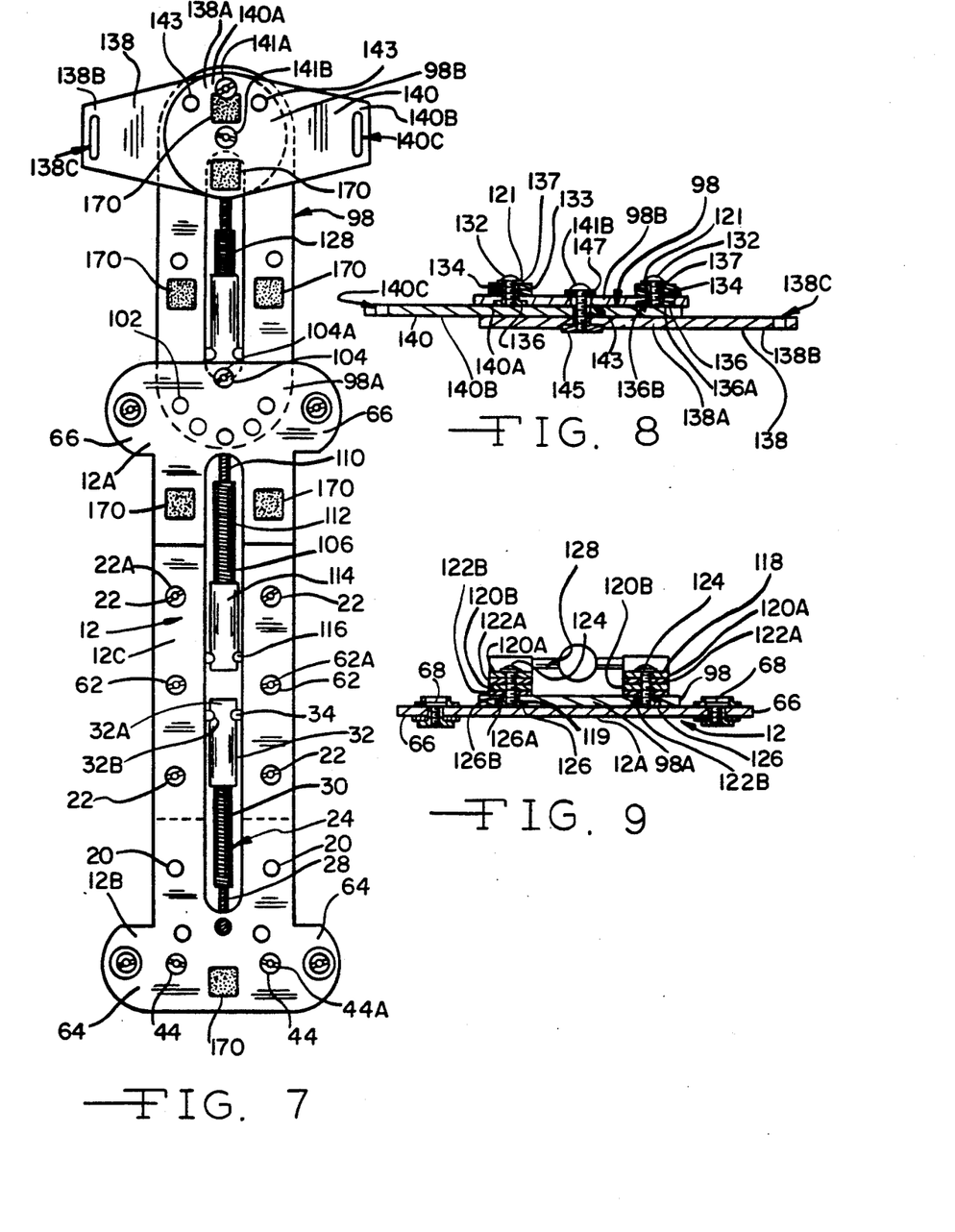
FIG. 7 is a front view of the support device 10 with the Velcro ® fasteners 170.
FIG. 8 is a cross-sectional view of FIG. 5 along the line 8—8 showing the right harness support 138 and the left harness support 140 with the fourth mounting bolts 132 and the fourth mounting nuts 136 and the central third attachment bolt 141B and third attachment nut 145.
FIG. 9 is a cross-sectional view of FIG. 5 along the line 9—9 showing the top end 12A of the first plate 12, the fasteners 68 on the distal harness tabs 66 and the third mounting bolts 124 of the second double bracket 118 and the third turnbuckle 128.

The first plate 12 has a top end 12A, a bottom end 12B and a central portion 12C and is secured to the torso 202 along the axis A—A which corresponds to the backbone of the person 200. As shown in FIG. 6, the first plate 12 has an outer plate 14 and an inner plate 16 which overlap in the central portion 12C of the first plate 12. In the preferred embodiment, the inner plate 16 and the outer plate 14 are identical in shape and contain the same holes such that only a single piece need be manufactured, thus allowing ease in manufacture. The inner plate 16 and outer plate 14 are generally elongate in shape with a square end and an enlarged rounded end. The inner and outer plates 16 and 14 are attached such that the similar square ends overlap in the central portion 12C of the first plate 12. Thus, the enlarged rounded end of the outer plate 14 forms the top end 12A of the first plate 12 and the enlarged rounded end of the inner plate 16 forms the bottom end 12B of the first plate 12 (FIG. 6). Preferably, the inner plate 16 and outer plate 14 are secured together by four first attachment bolts 18. The first attachment bolts 18 are inserted through first attachment holes 20 in the inner plate 16 and the outer plate 14. The first attachment bolts 18 are inserted first through the outer plate 14 and then through the inner plate 16. The first attachment bolts 18 are secured by first attachment nuts 22 which are mounted adjacent the side of the inner plate 16 adjacent the torso 202. In the preferred embodiment, the first attachment nuts 22 have a circular top portion with a tubular extension (not shown) extending perpendicular to the axis A—A through the first attachment hole 20. The circular top portion has a smooth outer surface with a notch 22A similar to a regular screw head (FIG. 7). This notch 22A enables the first attachment nuts 22 to be held stationary while the corresponding first attachment bolts 18 are removed or inserted. Preferably, a first attachment washer (not shown) is inserted between the head of the first attachment bolt 18 and the side of the first plate 12 opposite the torso 202. Preferably, the inner plate 16 and the outer plate 14 each contain extra first attachment holes 20 such that the length of the first plate 12 may be varied depending upon which first attachment holes 20 are used. By varying the length of the first plate 12 a wider variety of torsos 202 may be accommodated.

The outer plate 14 and inner plate 16 are moveable through use of a first turnbuckle 24 mounted on the side of the first plate 12 opposite the torso 202. The first turnbuckle 24 moves the inner plate 16 with respect to the central portion 12C of the first plate 12 which adjusts the shape of the first plate 12 such as to more closely follow contour of the back. Thus, allowing a more comfortable fit and less movement of the support device 10.

Figure 5:
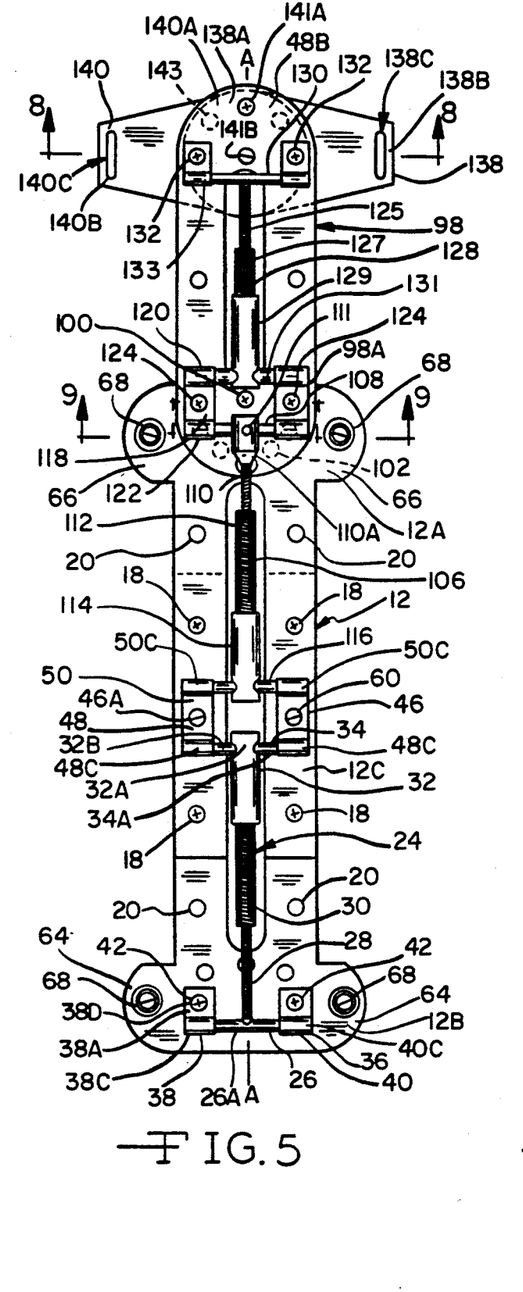
FIG. 5 is a back view of the support device 10 illustrating the first turnbuckle 24, the second turnbuckle 106 and the third turnbuckle 128.

As shown in FIG. 5, the first turnbuckle 24 consists of a first bottom cross bar 26, a first small threaded portion 28, a first large threaded portion 30, a first tubular receiving portion 32 and a first top cross bar 34. The first bottom cross bar 26 is mounted on the bottom end 12B of first plate 12 on the side opposite the torso 202. The first bottom cross bar 26 is mounted onto the first plate 12 by a first bracket 36. The first bracket 36 has a first left bracket 38 and a first right bracket 40 which are spaced an equal distance on opposite sides of the first turnbuckle 24 perpendicular to the axis A—A. The first left bracket 38 and the first right bracket 40 are preferably similar and therefore only one is described. The first left bracket 38 is preferably formed from a unitary piece and has an upper flap 38A and a lower flap 38B with a tubular holding portion 38C formed therebetween. In general, the first left bracket 38 is formed by bending the unitary piece around the tubular holding portion 38C such that the upper flap 38A is adjacent and on top of the lower flap 38B. A first mounting aperture 38D is located in the upper flap 38A and the lower flap 38B in the plane parallel to the axis A—A. A first mounting bolt 42 is inserted through the aperture 38D in the upper flap 38A and the lower flap 38B and through a first mounting hole (not shown) in the bottom end 12B of the first plate 12, such that the head of the first mounting bolt 42 is adjacent the upper flap 38A of the first left bracket 38. The first mounting bolt 42 is secured through the first mounting hole (not shown) by a first mounting nut 44, such that the first mounting nut 44 is adjacent the side of the first plate 12 adjacent the torso 202. In the preferred embodiment, the first mounting nut 44 is similar to the first attachment nuts 22 and has a circular top portion with a tubular extension (not shown) extending perpendicular to the axis A—A through the first mounting hole. The circular top portion has a smooth outer surface with a notch 44A similar to a regular screw head (FIG. 7). This notch 44A enables the first mounting nut 44 to be held stationary while the corresponding first mounting bolt 42 is removed or inserted. Preferably, a first mounting washer (not shown) is inserted between the head of the first mounting bolt 42 and the upper flap 38A of the first left bracket 38. The first left bracket 38 is mounted onto the first plate 12 such that the lower flap 38B of the first left bracket 38 is adjacent the side of the first plate 12 opposite the torso 202 and the tubular holding portion 38C extends perpendicular to the axis A—A with the upper flap 38A and the lower flap 38B extending outward from the tubular holding portion 38C toward the top end 12A of the first plate 12 parallel to the axis A—A.

The first bottom cross bar 26 is mounted through the first bracket 36 such that one end of the first bottom cross bar 26 is in the tubular holding portion 38C of the first left bracket 38 and the opposite end of the first bottom cross bar 26 is in the tubular holding portion 40C of the first right bracket 40. The enlarged central portion 26A of the first bottom cross bar 26 remains outside of the tubular holding portion 38C and 40C of the first left bracket 38 and the first right bracket 40 (FIG. 5). The diameter of the ends of the first bottom cross bar 26 is less than the diameter of the tubular holding portions 38C and 40C of the first left bracket 38 and first right bracket 40, such that the first bottom cross bar 26 rotates within the first bracket 36 during tensioning while preventing excessive movement of the first bottom cross bar 26.

The first small threaded portion 28 is mounted perpendicular to the first bottom cross bar 26 at preferably the center of the enlarged central portion 26A of the first bottom cross bar 26 (FIG. 5). In the preferred embodiment, the first small threaded portion 28 is welded onto the first bottom cross bar 26. The larger threaded portion 30 is threadably mated onto the end of the small threaded portion 28 opposite the first bottom cross bar 26 parallel to the axis A—A (FIG. 5).

The first tubular receiving portion 32 is threadably mated onto the end of the first large threaded portion 30 opposite the first small threaded portion 28. The first tubular receiving portion 32 extends upward from the first large threaded portion 30 toward the top end 12A of the first plate 12 parallel to the axis A—A. The distal end 32A of the first tubular receiving portion 32 opposite the first large threaded portion 30 has a first bore 32B which extends through the distal end 32A of the first tubular receiving portion 32 perpendicular to the axis A—A. The first top cross bar 34 is mounted through the first bore 32B in the distal end 32A of the first tubular receiving portion 32 perpendicular to the axis A—A. The diameter of the enlarged central portion 26A of the first top cross bar 34 is less than the diameter of the first bore 32B such that the first top cross bar 34 can rotate during tensioning within the first bore 32B but does not move excessively.

The first top cross bar 34 is mounted onto the first plate 12 by a first double bracket 46. The first double bracket 46 is formed from a first single bracket 48 and second single bracket 50 similar to the first bracket 36 described above. Thus, each single bracket 48 and 50 has a left bracket and a right bracket. The two single brackets 48 and 50 are mounted opposite each other such that the upper flaps 48A and 50A and lower flaps 48B and 50B of each single bracket 48 and 50 are layered adjacent to each other (FIG. 9). Thus, at least one flap of the first single bracket 48 is sandwiched between the flaps of the corresponding second single bracket 50. This formation required that only one pair of second mounting bolts 60 are needed to mount the first double bracket 46 onto the first plate 12. The second mounting bolts 60 are inserted through the apertures 46A in the flaps of the first and second single brackets 48 and 50 such that the tubular holding portions 48C and 50C of the first single bracket 48 and the second single bracket 50 are opposite with the upper flaps 48A and 50A and the lower flaps 48B and 50B of both single brackets 48 and 50 spaced therebetween. The second mounting bolts 60 are inserted through the aperture 46A and into the second mounting hole (not shown) and are secured in place by second mounting nuts 62 which are mounted adjacent the side of the first plate 12 adjacent the torso 202. In the preferred embodiment, the second mounting nuts 62 have a circular top portion with a tubular extension (not shown) extending perpendicular to the axis A—A through the second mounting hole. The circular top portion has a smooth outer surface and a notch 62A across the top similar to the regular screw top. This notch 62A enables the second mounting nut 62 to be held stationary while the corresponding second mounting bolt 60 is removed or inserted (FIG. 7). Preferably, a second mounting washer (not shown) is inserted between the head of the second mounting bolt 60 and the upper flap 48A and 50A of the first double bracket 46. The first double bracket 46 reduces the number of second mounting bolts 60, second mounting nuts 62 and second mounting holes thus reducing cost and also space needed on the first plate 12.

The first top cross bar 34 is mounted through the first double bracket 46 such that one end of the first top cross bar 34 is in the tubular holding portion 48C of the first single bracket 48 and the opposite end of the first top cross bar 34 is in the opposite tubular holding portion 48C of the same first single bracket 48. The enlarged central portion 34A of the first top cross bar 34 remains outside of the first double bracket 46 between the two tubular holding portions 48C of the first single bracket 48 (FIGS. 5 and 6). The diameter of the ends of the first top cross bar 34 is less than the diameter of the tubular holding portions 48C of the first single bracket 48. The smaller diameter of the ends is such that the first top cross bar 34 rotates within the first double bracket 46 during tensioning but not so as to allow excessive movement of the first top cross bar 34. The first double bracket 46 is mounted onto the first plate 12 in the central portion 12C of the first plate 12 where the inner plate 16 and the outer plate 14 overlap. Thus, the first turnbuckle 24 is mounted between the bottom end 12B of the first plate 12 and the central portion 12C of the first plate 12. This positioning of the first turnbuckle 24 allows the bottom end 12B of the first plate 12 to be moved with respect to the central portion 12C of the first plate 12. This variation of only a portion of the first plate 12 allows for a more contoured fit to the back.

The first plate 12 is preferably elongate in shape having proximal harness tabs 64 located at the bottom end 12B on the inner plate 16 and distal harness tabs 66 located at the top end 12A on the outer plate 14 (FIG. 5). The proximal harness tabs 64 and distal harness tabs 66 extend outward perpendicular to the axis A—A from both sides of the bottom end 12B and top end 12A of the first plate 12. The proximal harness tabs 64 and the distal harness tabs 66 contain a portion of a fastener 68 on the side of the support device 10 adjacent the torso 202 which corresponds to an opposite portion of a fastener 68 on the torso harness 70 (to be described in detail hereinafter) (FIG. 5). Preferably, the proximal harness tabs 64 and the distal harness tabs 66 have rounded corners to prevent possible injury during use of the support device 10.

Figure 2:
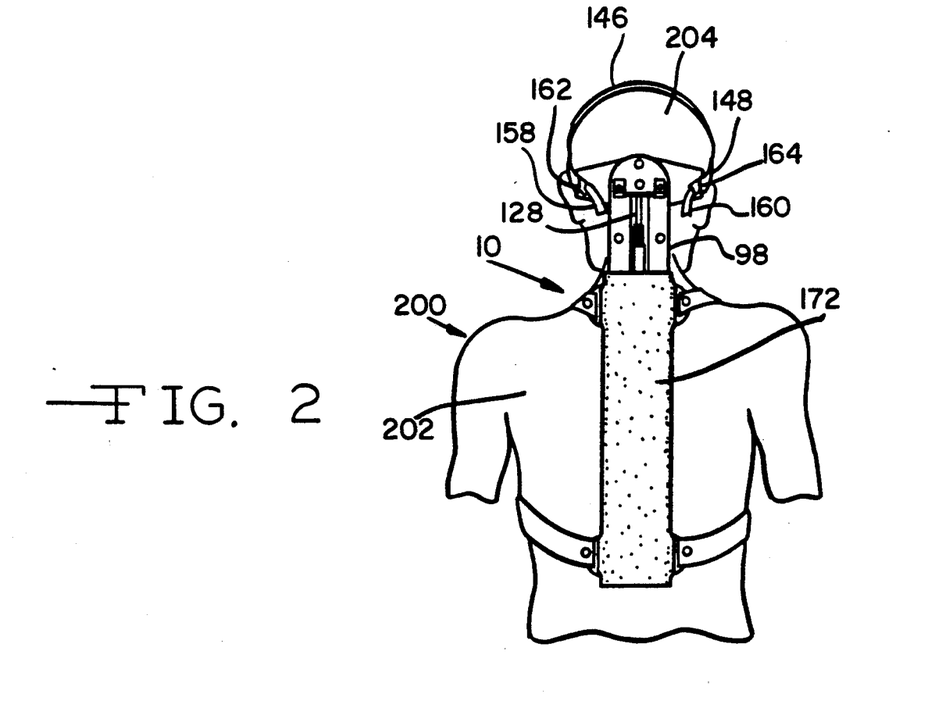
FIG. 2 is a back view of the support device 10 being worn by a person 200.
Figure 4:
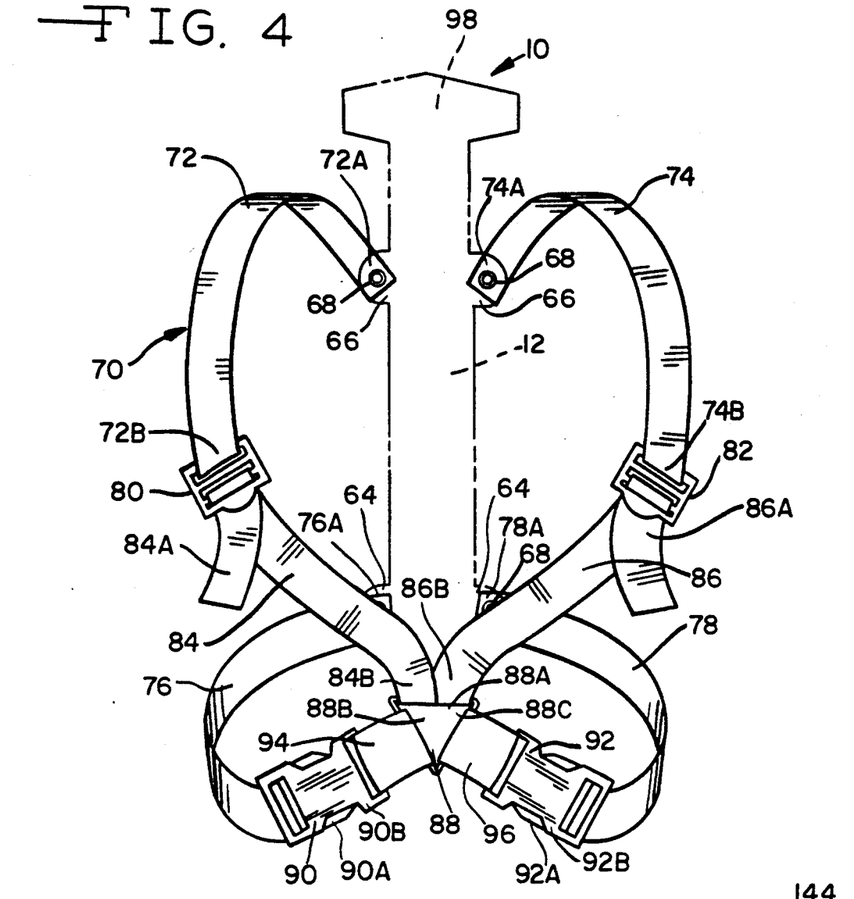
FIG. 4 is a front view of the support device 10 showing the attachment of the torso harness 70 around the front of the person 200 (not shown).

As shown in FIG. 4, the first plate 12 is secured onto the torso 202 by a torso harness 70. The first plate 12 is positioned along the back such that the proximal harness tabs 64 are adjacent the lower back and the distal harness tabs 66 are adjacent the upper back, preferably below the neck area (FIG. 2). The torso harness 70 has a first upper strap 72 and a second upper strap 74 and a first lower strap 76 and a second lower strap 78. The first and second upper straps 72 and 74 each have a first end 72A and 74A which contain a portion of a fastener 68. The first end 72A and 74A of the first and second upper straps 72 and 74 is fastened onto the opposite portion of the corresponding fastener 68 on one of the distal harness tabs 66. The first and second lower straps 76 and 78 also contain a first end 76A and 78A which contains a fastener 68. The first end 76A and 78A of the first and second lower straps 76 and 78 is fastened onto the opposite portion of the corresponding fastener 68 on one of the proximal harness tabs 64. In the preferred embodiment, both sets of fasteners 68 are similar and are in the form of a snap. The ends of the straps are snapped onto the distal and proximal harness tabs 64 and 66 on the side of the first plate 12 adjacent the torso 202 for easy removal of the torso harness 70.

The second ends 72B and 74B of the first and second upper straps 72 and 74 are permanently attached to a first and second loop buckles 80 and 82. A first middle strap 84 and a second middle strap 86 extend between the first and second loop buckles 80 and 82 and a first side 88A of the triangular center holder 88. The first ends 84A and 86A of the first and second middle straps 84 and 86 are permanently attached to the triangular center holder 88 and the second ends 84B and 86B of the first and second middle straps 84 and 86 are threaded through the first and second loop buckles 80 and 82. Although not permanently attached, the second end 84B and 86B of the first and second middle straps 84 and 86 are doubled in thickness by folding over the ends such as to make removal of the second ends 84B and 86B from the loop buckles 80 and 82 difficult and to prevent unintentional removal.

A first and second male coupler 90A and 92A of a first and second lock fit fastener 90 and 92 are slideably attached to the first and second lower straps 76 and 78 (FIG. 4). The second ends 72B and 74B of the first and second lower straps 76 and 78 are folded over to increase the thickness and prevent the first and second male coupler 90A and 92A from unintentionally sliding off the first and second lower straps 72 and 74. The first and second female coupler 90B and 92B of the first and second lock fit fasteners 90 and 92 are permanently attached to a second side 88B and third side 88C of the triangular center holder 88. The first and second female couplers 90B and 92B are permanently attached to the triangular center holder 88 by a first and second connector strap 94 and 96 which are of a length such as to secure the first and second female couplers 90B and 92B of the lock fit fasteners 90 and 92 to the triangular center holder 88. In the preferred embodiment, flexible nylon straps are used to attach the first and second female coupler 90B and 92B to the triangular center holder 88 so as to allow some flexible movement of the first and second female coupler 90B and 92B.

As seen in FIGS. 1 and 2, the support device 10 is strapped to the torso 202 by the torso harness 70 such that the first and second upper straps 72 and 74 extend from the distal harness tabs 66 over the shoulders of the person 200. The first and second middle straps 84 and 86 then extend downward from the loop buckles 80 and 82 of the first and second upper strap 72 and 74 toward the center of the torso 202 to the triangular center holder 88. The first and second lower straps 76 and 78 extend from the proximal harness tabs 64 around approximately about the center of the sides of the torso 202. The first and second lower straps 76 and 78 extend around to the front side of the torso 202 where the first and second male couplers 90A and 92A are inserted into the first and second female couplers 90B and 92B of the lock fit fasteners 90 and 92. FIG. 4 shows the torso harness 70 fully connected without the person 200. The torso harness 70 is preferably constructed of nylon straps which are strong and yet lightweight. In the preferred embodiment, the first and second lower straps 76 and 78 are wider than the first and second upper straps 72 and 74 in order to provide more strength as well as better comfort.

The bendable second plate 98 of the support device 10 has a proximal end 98A and a distal end 98B and is mounted onto the first plate 12 such that the proximal end 98A of the second plate 98 overlaps and is attached to the top end 12A of the first plate 12. The second plate 98 extends upward from the first plate 12 parallel to the axis A—A adjacent the rear portion of the head 204. In the preferred embodiment, the second plate 98 is elongate in shape with rounded ends to allow uninterfered turning at the proximal end 98A and to prevent possible injury due to sharp corners at both the proximal end 98A and the distal end 98B. As shown in FIG. 1, the proximal end 98A of the second plate 98 is mounted onto the top end 12A of the first plate 12 by two second attachment bolts 100 (one shown). The two second attachment bolts 100 are inserted through second attachment holes 102 in the first plate 12 and the second plate 98. The second attachment bolts 100 may be inserted through the first plate 12 and second plate 98 in either order depending upon whichever way is easiest for removal and insertion of the second attachment bolts 100. In the preferred embodiment, the second attachment nuts 104 have a circular top portion with a tubular extension (not shown) extending perpendicular to the axis A—A through the second attachment hole 102. The circular top portion has a smooth outer surface with a notch 104A across the top similar to a regular screw head. This notch 104A enables the second attachment nuts 104 to be held stationary while the corresponding second attachment bolts 100 are removed or inserted. Preferably, a second attachment washer (not shown) is mounted between the head of the second attachment bolt 100 and the first or second plate 12 and 98 depending on the direction of insertion of the second attachment bolt 100. The second attachment bolts 100 are secured by second attachment nuts 104 which are mounted adjacent either the first plate 12 or the second plate 98 depending upon the insertion of the second attachment bolts 100. The second attachment bolts 100 are smaller in diameter than the second attachment holes 102 such as to allow the second attachment bolts 100 to move side-to-side within the second attachment holes 102. This slight movement allows the second plate 98 to pivot, thus increasing the adjustability of the second plate 98 with respect to the back and neck 206. In the preferred embodiment, the proximal end 98A of the second plate 98 and the top end 12A of the first plate 12 have several extra coordinating second attachment holes 102 formed in a semi-circle. Thus, the positioning of the second plate 98 onto the first plate 12 may be angled to the right or left from the axis A—A. This allows better positioning of the support device 10 to correspond to the particular inclination of the torso 202, the neck 206 and the head 204.

The first plate 12 and second plate 98 are also connected together by a second turnbuckle 106 mounted on the proximal end 98A of the second plate 98 and the top end 12A of the first plate 12 on the side opposite the torso 202. The second turnbuckle 106 is similar to the first turnbuckle 24 previously described and is comprised of a second bottom cross bar 108, a second small threaded portion 110, a second large threaded portion 112, a second tubular receiving portion 114 and a second top cross bar 116. The second turnbuckle 106 is mounted opposite from the first turnbuckle 24 such that the second top cross bar 116 is mounted within the first double bracket 46 opposite the first top cross bar 34 of the first turnbuckle 24.

The second turnbuckle 106 extends upward from the first double bracket 46 parallel to the axis A—A toward the top end 12A of the first plate 12 and the proximal end 98A of the second plate 98. The second small threaded portion 110, second large threaded portion 112 and second tubular receiving portion 114 are mounted with respect to each other identical to the first turnbuckle 24 except for their overall opposite attachment. The proximal end 110A of the second small threaded portion 110 opposite the end mounted to the second large threaded portion 112 has been modified from the first turnbuckle 24 such as to allow the pivotal motion of the second plate 98 around the second attachment bolts 100 (one shown). The proximal end 110A of the second small threaded portion 110 of the second turnbuckle 106 has a U-shaped end 110B which has a width greater than the diameter of the second top cross bar 116. The second top cross bar 116 is inserted in the U-shaped end 110B such that the legs 110C of the U-shaped end 110B extend above and below the second top cross bar 116 (FIG. 6). A pin 111 is then inserted through the legs 110C of the U-shaped end 110B and the second top cross bar 116 to secure the cross bar 116 while allowing pivotal movement as well as the standard upward rotational movement of the second turnbuckle 106. In the preferred embodiment, the legs 110C of the U-shaped end 110B are tapered toward the junction where the U-shaped end 110B is mounted onto the second small threaded portion 110 (FIG. 6). This tapering of the U-shaped end 110B prevents the U-shaped end 110B of the second small threaded portion 110 of the second turnbuckle 106 from contacting the proximal end 98A of the second plate 98 during tensioning.

The second bottom cross bar 108 of the second turnbuckle 106 is mounted in a second double bracket 118 opposite the third top cross bar 131 of the third turnbuckle 128 (to be described in detail hereinafter). The second double bracket 118 is mounted onto the proximal end 98A of the second plate 98 where the first plate 12 and second plate 98 overlap. The second double bracket 118 is mounted similar to the first double bracket 46 with the upper and lower flaps 120A, 122A and 120B, 122B of the two single brackets 120 and 122 alternately layered, and thus the third mounting bolts 124 extend through apertures 121 in the layers of upper and lower flaps 120A, 122A and 120B, 122B (FIG. 6). The third mounting bolts 124 of the second double bracket 118 are mounted through a third mounting hole 119 only in the second plate 98 in order to allow the first plate 12 and the second plate 98 to move independent of each other. The third mounting bolts 124 are secured by third mounting nuts 126 which are mounted adjacent the opposite side of the second plate 98 from where the second double bracket 118 is mounted. As seen in FIG. 9, the third mounting nuts 126 have a circular top portion 126A and a tubular extension 126B extending perpendicular to the axis A—A through the third mounting hole 119. The third mounting nuts 126 are preferably similar to those previously described and are mounted flush with the surface of the second plate 98 thus decreasing the interference and friction between the third mounting nuts 126 and the first plate 12 during movement (FIG. 9).

The second plate 98 also has a third turnbuckle 128 connected between the proximal end 98A and the distal end 98B. The third turnbuckle 128 is similar to the first turnbuckle 24 on the first plate 12 and is mounted onto the second plate 98 in a similar manner. The third top cross bar 131 is mounted through the second double bracket 118 opposite the second bottom cross bar 108. The third tubular receiving portion 129, third large threaded portion 127 and third small threaded portion 125 extend upward parallel to the axis A—A in a direction similar to the second turnbuckle 106. The third bottom cross bar 130 is mounted onto the distal end 98B of the second plate 98 where the right harness support 138 and left harness support 140 (to be described in detail hereinafter) overlap. The third bottom cross bar 130 is mounted onto the second plate 98 by a second bracket 133 similar to the first bracket 36 of the first turnbuckle 24. The second bracket 133 is mounted onto the distal end 98B of the second plate 98 similar to the first bracket 36. The fourth mounting bolts 132 are inserted through fourth mounting holes 134 in the second plate 98 only. The fourth mounting bolts 132 are secured by fourth mounting nuts 136 which are mounted adjacent the side of the second plate 98 opposite the second bracket 133. In the preferred embodiment, the fourth mounting nuts 136 have a circular top portion 136A with a tubular extension 136B extending perpendicular to the axis A—A through the fourth mounting hole 134. The circular top portion 136A has a smooth outer surface with a notch (not shown) across the top similar to a regular screw head. This notch enables the fourth mounting nut 136 to be held stationary while the corresponding fourth mounting bolt 132 is removed or inserted (FIG. 7). As shown in FIG. 8, the fourth mounting nuts 136 are preferably mounted such that the circular top portion 136A is flush with the surface of the second plate 98 in order to avoid interference between the fourth mounting nuts 136 and either the right harness support 138 or the left harness support 140 depending on their mounting order. Preferably, a fourth mounting washer 137 is inserted between the head of the fourth mounting bolt 132 and the upper flap of the second bracket 133. The third turnbuckle 128 allows adjustment of the contour of the second plate 98 so as to achieve a better and more comfortable fit to the head 204 and neck 206.

A right harness support 138 and a left harness support 140 extend from opposite sides of the distal end 98B of the second plate 98 perpendicular to the axis A—A. The right harness support 138 and left harness support 140 are preferably two separate pieces which are secured together and onto the distal end 98B of the second plate 98 by an upper third attachment bolt 141A and a central attachment bolt 141B which are inserted through an upper third attachment hole 143 and a central third attachment hole (not shown) in the right harness support 138, left harness support 140 and the second plate 98 (FIG. 8). In the preferred embodiment, the right harness support 138 and the left harness support 140 have extra upper third attachment holes 143 positioned in a semi-circle in order that the positioning of the right harness support 138 and left harness support 140 may be adjusted. The proximal end 98A and the distal end 98B of the second plate 98 have identical holes such that the ends may be interchangeable. However, in the preferred embodiment, the proximal end 98A is more rounded to provide less interference with the first plate 12, thus making the proximal end 98A and distal end 98B distinct from each other. In an alternate embodiment, the distal end 98B of the second plate 98 can be further rounded to match the proximal end 98A to make the proximal end 98A and distal 98B identical and interchangeable in order to reduce manufacturing costs. The extra upper third attachment holes 143 are located such that the right and left harness supports 138 and 140 may be pivoted up or down independently around the central third attachment bolt 141B. The pivoting of the right and left harness supports 138 and 140 is intended to accommodate any natural inclination of the head 204 on the neck 206.

The upper and central third attachment bolts 141A and 141B are inserted first through the second plate 98 and then through either the right harness support 138 or the left harness support 140 whichever is mounted adjacent the second plate 98. As both harness supports are identical, mounting order is not important. The upper and central third attachment bolts 141A and 141B are secured by third attachment nuts 145 which are mounted adjacent either the right harness support 138 or the left harness support 140 whichever is adjacent the rear portion of the head. The third attachment nut 145 is preferably identical to those previously described. In the preferred embodiment, the third attachment washer 147 is inserted between the head 204 of the upper and central third attachment bolts 141A and 141B and the second plate 98. Additionally, as seen with the attachment of the first plate 12 and the second plate 98, the diameter of the upper and central third attachment bolts 141A and 141B is slightly less than the diameter of the third attachment holes 143. This allows the upper and central third attachment bolts 141A and 141B to move slightly, thus allowing movement of the right harness support 138 and the left harness support 140. The slight independent movement of the right and left harness supports 138 and 140 enables the support device 10 to be more adjustable. In the preferred embodiment, the right harness support 138 and the left harness support 140 are identical in size and shape. The right and left harness supports 138 and 140 have a circular end 138A and 140A and a smaller square end 138B and 140B. In the preferred embodiment, the circular end 138B and 140B is identical in shape and size to the proximal end 98A of the second plate 98. The circular end 138A of the right harness support 138 and the left harness support 140 allow the right and left harness support to rotate around the central attachment bolt 141B without exposing sharp corners. The square end 138B and 140B of the right harness support 138 and the left harness support 140 extend outward from their circular ends 138A and 140A perpendicular to the axis A—A with the sides of the right and left harness supports 138 and 140 angled toward each other such that the square end portion 138A is smaller in size than the diameter of the circular portion 138A and 140A. Each of the square end portions 138B and 140B of the right and left harness supports 138 and 140 have slots 138C and 140C extending parallel to the axis A—A which are used to secure the head harness 142 to the support device 10.

Figure 3:
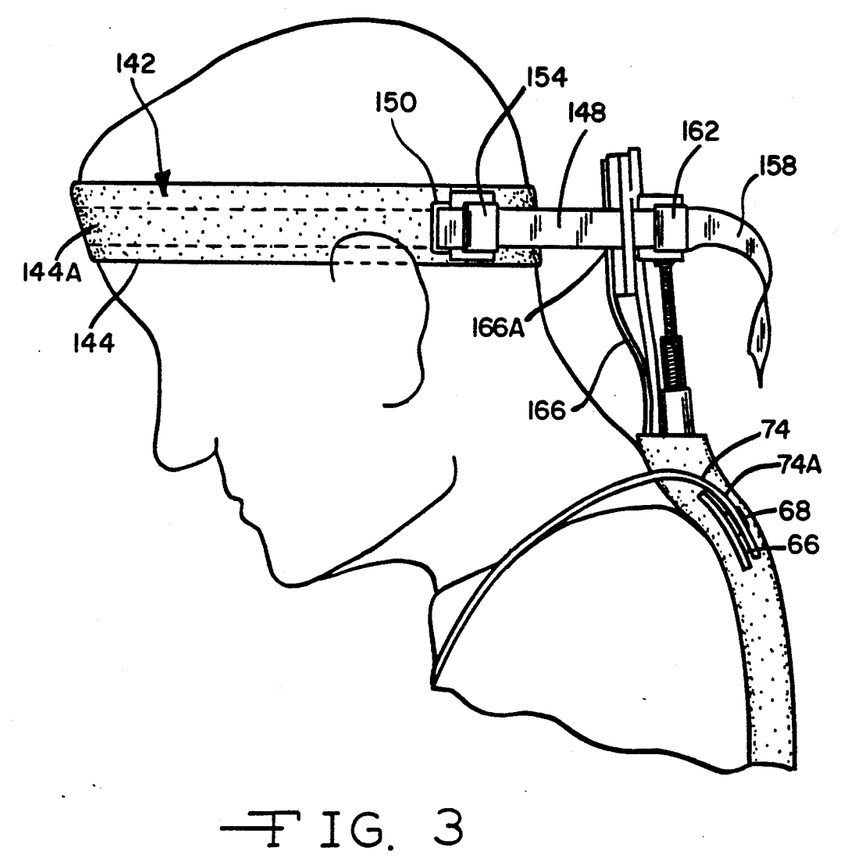
FIG. 3 is a side view showing the head harness 142 on the person 200 and attached to the second plate 98 by the tether 148.
Figure 10:
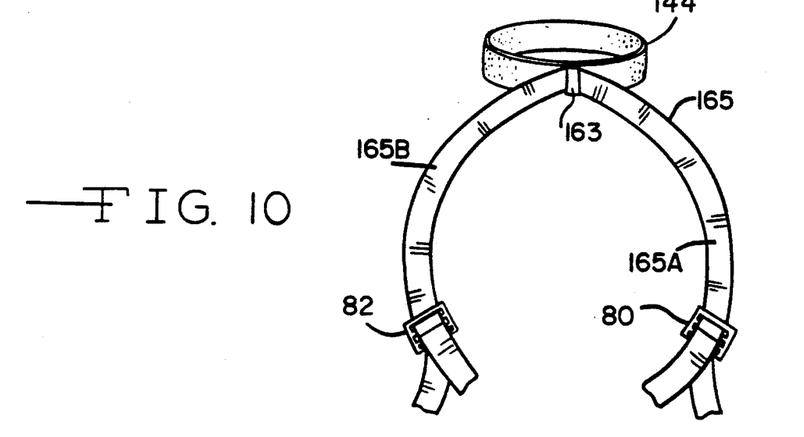
FIG. 10 is a back view of the head band 144 showing the loop 163 and the positioning strap 165.

As shown in FIG. 3, the head harness 142 consists of a head band 144 with a crown strap 146 and a tether 148 which secures the head band 144 to the support device 10 to support the head 204. The head band 144 is of a size to fit around the head 204 of the person 200. The front portion 144A of the head band 144 is hollow such as to allow the tether 148 to be slideably mounted through the head band 144, such that the head 204 is able to rotate from side to side while maintaining a desired head position (FIG. 3). The positioning of the tether 148 inside the front portion 144A of the head band 144, also camouflages the tether 148 and thus makes the support device 10 less noticeable. The tether 148 is mounted into a first eyelet 150 through the front portion of the head band 144 and out a second eyelet (not shown) on the opposite side of the head band 144. A first stop buckle 154 and a second stop buckle (not shown) are mounted onto the tether 148 on either side of the head 204 adjacent the outside of the first and second eyelets 150. The first and second stop buckles 154 are used to adjust the size of the head band 144 to the head 204. This assures that the tether 148 is properly placed on either side of the head 204, thus ensuring pulling pressure is applied at the appropriate points. The tether 148 extends outward from the first and second eyelets 150 on either side of the head band 144. A right tether end 158 and a left tether end 160 are each inserted respectively, through the slots 138C and 140C in the right and left harness support 138 and 140 entering the slot 138C and 140C from the side adjacent the neck. A third stop buckle 162 and a fourth stop buckle 164 are mounted on the right and left tether ends 158 and 160 and adjacent the side of the right and left harness support 138 and 140 opposite the neck 206. The third and fourth stop buckle 162 and 164 allow the head harness 142 to be tightened and held such as to hold the head 204 in a desired position. The head harness 142 also has a crown strap 146 which positions the head band 144 in the desired position around the head 204 and also prevents the head band 144 from slipping. As seen in FIG. 10, the head band 144 has a loop 163 located at the back of the head 204 on the side of the head band 144 opposite the back of the head 204. A positioning strap 165 having a first end 165A and a second end 165B is inserted through the loop 163 of the head band 144. The first end 165A and second end 165B extend outward from either side of the loop 163 and over the shoulders of the person 200. The first end 165A of the positioning strap 165 is then inserted into the first loop buckle 80 of the torso harness 70 and accordingly the second end 165B of the positioning strap 165 is inserted into the second loop buckle 82 of the torso harness 70. The first and second end 165A and 165B of the positioning strap 165 are inserted into the first and second loop buckle 80 and 82 in order that the positioning strap 165 may be held at a selected tautness. The positioning strap 165 is intended to pull downward on the back of the head band 144 such as to prevent the head band 144 from moving upward on the back of the head 204. In the preferred embodiment, the support device 10 and the head harness 142 are positioned such that the tether 148 pulls the head 204 backwards at the head's center of gravity (FIG. 3). The head harness 142 and tether 148 allow the head 204 to rotate while maintaining a desired head position. Preferably, the head band 144 is constructed of an elastic type material with a padded inner side to provide comfort. The crown strap 146 is preferably provided with Velcro ® to make adjustments of the height of the head band 144 easier.

As shown in FIG. 3, a first pad 166 is provided between the first plate 12 and the second plate 98 on the side adjacent the neck 206 and head 204. The first pad 166 is intended to cover the second and upper and central third attachment bolts 100, 141A and 141B or the second and third attachment nuts 104 and 145 depending upon how the bolts are mounted in the proximal and distal ends 98A and 98B of the second plate 98, in order to provide further comfort for the person 200. The first pad 166 also has a head pad 166A over the distal end 98B of the second plate 98, thus providing additional padding for the head 204 if contact is made between the head 204 and the support device 10. The first pad 166 is preferably elongate in shape with rounded ends similar to the second plate 98 and the head pad 166A is preferably circular and formed as a single unitary piece with the first pad 166. A second pad (not shown) extends the length of the first plate 12 to the portion of the support device 10 where the first plate 12 and second plate 98 overlap, which is covered by the first pad 166. The second pad is intended to cover the first mounting nuts 44 and the second mounting nuts 62 for the first and second turnbuckles 24 and 106 and the first attachment nuts 22 for the inner and outer plates 14 and 16. The second pad provides cushion between the back and the support device 10. In the preferred embodiment, both the first pad 166 and the second pad are secured onto the support device 10 by Velcro ® fasteners 170 which allow for easy removal and replacement (FIG. 7).

Finally as shown in FIG. 2, a cover 172 extends around the entire first plate 12 excluding the portion where the first plate 12 and second plate 98 overlap. The cover 172 has tab holes 172A for the proximal harness tabs 64 and the distal harness tabs 66. In the preferred embodiment, the cover 172 is constructed from a rubber like material and secured around the first plate 12 by Velcro ® along the entire length of the cover 172 adjacent the torso 202. The cover 172 is intended to cover the support device 10 such as to make the support device 10 less noticeable when being worn.

The first support device 10 is adjusted in any of a number of ways in order to fit the person 200. The length of the first plate 12 can be adjusted to accommodate the length of the torso 202. The positioning of the second plate 98 onto the first plate 12 as well as the right harness support 138 and left harness support 140 on the second plate 98 can be changed to accommodate any inclination of the neck 206 and head 204. The contour of the support device 10 is also adjusted by a first, second and third turnbuckle 24, 106 and 128 in order to accommodate the contour of the torso 202, neck 206 and head 204. After being adapted for the particular user, the support device 10 is strapped onto the torso 202 by the torso harness 70, such that the first plate 12 is positioned along the backbone of the person 200 and the second plate 98 is behind the neck 206 and head 204. The head 204 of the person 200 is attached to the support device 10 by the head harness 142 which maintains the head 204 in a desired position while allowing the head 204 to rotate.

It will appreciated that the second plate 98 can be bent to accommodate the curvature of the neck 206.

With most persons the curvature shown in FIGS. 1 and 3 is usually more pronounced than shown.

It is intended that the foregoing description be only illustrative of the present invention and that the present invention be limited only by the hereinafter appended claims.

I claim:

1. A head harness means for a head support device to be worn by a person to maintain a desired head position relative to a support means which is mounted on the torso of a person to which the head harness means is secured, which comprises:

a headband having a pocket therein, a harness slidably mounted in said pocket and a tether means connected to the harness adjacent the center of gravity of the person's head and adapted to be connected to a support means, so that the tether means supports the head in a desired position and so that the person's head can be moved side to side on his neck.

2. The head harness means of claim 1 wherein the tether means enables the head to rotate on the neck while maintaining the desired head position.

3. The head harness means of claim 2 further including a second band mounted on the headband adapted to extend over the top of the head.

4. The head harness means of claim 3 further including a positioning strap mounted on the back of the headband for holding the head harness means down on the head.

5. The head harness means of claim 2 wherein a stop buckle is provided on the tether which engages the headband to limit the side to side movement of the head.

6. The head harness means of claim 1 further including a second band mounted on the headband adapted to extend over the top of the head.

7. The head harness means of claim 1 further including a positioning strap mounted on the back of the headband for holding the head harness means down on the head.

8. The head harness means of claim 1 wherein a stop buckle is provided on the tether which engages the headband to limit the side to side movement of the head.

* * * * *